(12) United States Patent
von Ilberg

(10) Patent No.: US 6,231,604 B1
(45) Date of Patent: May 15, 2001

(54) APPARATUS AND METHOD FOR COMBINED ACOUSTIC MECHANICAL AND ELECTRICAL AUDITORY STIMULATION

(75) Inventor: Christoph von Ilberg, Frankfurt am Main (DE)

(73) Assignee: Med-El Elektromedizinische Gerate Ges.m.b.H, Innsbruck (AT)

(*) Notice: Subject to any disclaimer, the term of this patent is extended or adjusted under 35 U.S.C. 154(b) by 0 days.

(21) Appl. No.: 09/258,997

(22) Filed: Feb. 26, 1999

Related U.S. Application Data
(60) Provisional application No. 60/076,381, filed on Feb. 26, 1998.

(51) Int. Cl.⁷ ....................................................... A61F 2/18
(52) U.S. Cl. ............................................................... 623/10
(58) Field of Search ............................. 623/10; 607/57; 381/68

(56) References Cited

U.S. PATENT DOCUMENTS

| | | | |
|---|---|---|---|
| 2,995,633 | * | 8/1961 | Puharich et al. ..................... 179/107 |
| 3,751,605 | * | 8/1973 | Michelson ............................ 179/107 |
| 3,752,939 | * | 8/1973 | Bartz .................................... 179/107 |
| 4,957,478 | * | 9/1990 | Maniglia ................................ 600/25 |
| 5,015,224 | * | 5/1991 | Maniglia ................................ 600/25 |
| 5,951,601 | * | 9/1999 | Lesinki et al. ......................... 623/10 |
| 5,991,663 | * | 11/1999 | Irlicht et al. ............................ 607/57 |

* cited by examiner

Primary Examiner—David H. Willse
Assistant Examiner—Hieu Phan
(74) Attorney, Agent, or Firm—Bromberg & Sunstein LLP

(57) ABSTRACT

A hearing prosthesis is described for a user in an acoustic environment having a range of audio frequencies. The prosthesis includes an electrical stimulation module, and acoustic mechanical stimulation module, and a stimulation amplifier. The electrical stimulation module delivers to the auditory nerve of the user an electrical stimulation signal representative of a first subrange of frequencies in the range of audio frequencies in the acoustic environment. The acoustic mechanical stimulation module delivers to the inner ear structure of the user a mechanical stimulation signal representative of a second subrange of frequencies in the range of audio frequencies in the acoustic environment. The stimulation amplifier in communication with the electrical stimulation module and the acoustic mechanical stimulation module that determines, for each stimulation module, an amplification magnitude envelope for the subrange of frequencies for that stimulation module.

30 Claims, 3 Drawing Sheets

APPARATUS AND METHOD FOR COMBINED ACOUSTIC MECHANICAL AND ELECTRICAL AUDITORY STIMULATION

This application claims the benefit of U.S. Provisional Application No. 60/076,381, filed Feb. 26, 1998. This application is incorporated herein by reference.

TECHNICAL FIELD

The present invention relates to the structure and method of operation of a hearing prosthesis.

BACKGROUND ART

Approximately 5 to 10% of the population suffer from impaired hearing. The degree of hearing loss ranges from mild, to moderate, to severe, to profound hearing losses on the verge of deafness, and finally, to acquired or congenital deafness. The cause for such hearing losses can lie in the region of the ear which conducts the sound wave (ear drum, middle ear), in the inner ear (cochlea), or in the auditory nerve or central auditory processing. Depending upon the cause, site, and degree of hearing difficulty, operative therapy, rehabilitation, drug therapy, or other therapies may be indicated. When these therapies are insufficient or unsuccessful, there are a variety of technical hearing aids (auditory prosthesis) available in order to improve hearing.

In the prior art, hearing aids have been based on one of two basically different principles: acoustic mechanical stimulation, or electrical stimulation. With acoustic mechanical stimulation, sound is amplified in various ways and delivered to the inner ear as mechanical energy. This may be through the column of air to the ear drum, or direct delivery to the ossicles of the middle ear. Acoustic mechanical stimulation requires that the structure of the cochlea, hair cells, and auditory nerve all be intact. The more hair cells which are destroyed or not functioning properly, the less effective is acoustic mechanical stimulation.

Electrical stimulation functions very differently. With this method, used when the structures of the cochlea-in particular, the hair cells—are disrupted, the sound wave is transformed into an electrical signal. The resulting stimulation pattern can be "understood" by the auditory nerve. Electrical stimulation does not require that the structure of the cochlea and the hair cells be intact. It is only necessary that the auditory nerve, as well as the central processing centers, are sufficiently intact. With electrical stimulation, the stimulating electrodes should be placed as close as possible to the nerve endings of the auditory nerve. This occurs optimally when an electrode carrier is inserted into the cochlea. As a rule, this procedure results in destruction of the structures of the inner ear which may still be functioning. Therefore, this technique is not used when there is significant residual hearing.

SUMMARY OF THE INVENTION

A preferred embodiment of the present invention provides a hearing prosthesis for a user in an acoustic environment having a range of audio frequencies. The prosthesis includes a microphone, an electrical stimulation module, and an acoustic mechanical stimulation module. The microphone converts the sounds of the acoustic environment into a representative electrical signal output The electrical stimulation module is responsive to the representative electrical signal and delivers to the auditory nerve of the user an electrical stimulation signal representative of a first subrange of frequencies in the range of audio frequencies in the acoustic environment. The acoustic mechanical stimulation module is responsive to the representative electrical signal and delivers to the inner ear structure of the user a mechanical stimulation signal representative of a second subrange of frequencies in the range of audio frequencies in the acoustic environment.

The electrical stimulation module may use analog signal processing, or digital signal processing, eg., continuous interleaved sampling (CIS), to produce the electrical stimulation signal Ball-shaped or cone-shaped electrodes having a fixation collar may be used to deliver the electrical stimulation signal from either an extracochlear position, from a cochleostomy window. Alternatively, multichannel array electrodes may be partially or fully inserted into the cochlea of the user to deliver the electrical stimulation signal. The acoustic mechanical stimulation module also may use either analog or digital signal processing to produce the mechanical stimulation signal. An embodiment may further include a stimulation amplifier that amplifies the representative electrical signal output from the microphone for input to the stimulation modules.

A preferred embodiment also includes a method of a hearing prosthesis system for processing sounds in an acoustic environment having a range of audio frequencies. The method includes converting, with a microphone, the sounds of the acoustic environment into a representative electrical signal output; delivering to the auditory nerve of a user, an electrical stimulation signal from an electrical stimulation module responsive to the representative electrical signal, the electrical stimulation signal representative of a first subrange of frequencies in the range of audio frequencies in the acoustic environment; and delivering to the inner ear structure of the user, a mechanical stimulation signal from an acoustic mechanical stimulation module responsive to the representative electrical signal, the mechanical stimulation signal representative of a second subrange of frequencies in the range of audio frequencies in the acoustic environment The electrical stimulation signal may be produced by the electrical stimulation module using analog signal processing, or digital signal processing, e.g., continuous interleaved sampling (CIS). The electrical stimulation module may deliver the electrical stimulation signal using ball-shaped or cone-shaped electrodes having a fixation collar from either an extracochlear position, or a cochleostomy window. alternatively, multichannel array electrodes may be partially or fully inserted into the cochlea of the user. The mechanical stimulation signal may be produced by the acoustic mechanical stimulation module using either analog or digital signal processing. The method may also further include amplifying the representative electrical signal output from the microphone with a stimulation amplifier for input to the stimulation modules.

BRIEF DESCRIPTION OF THE DRAWINGS

The invention will be more readily understood by reference to the following description, taken with the accompanying drawings, in which.

DETAILED DESCRIPTION OF SPECIFIC EMBODIMENTS

Figure 1:
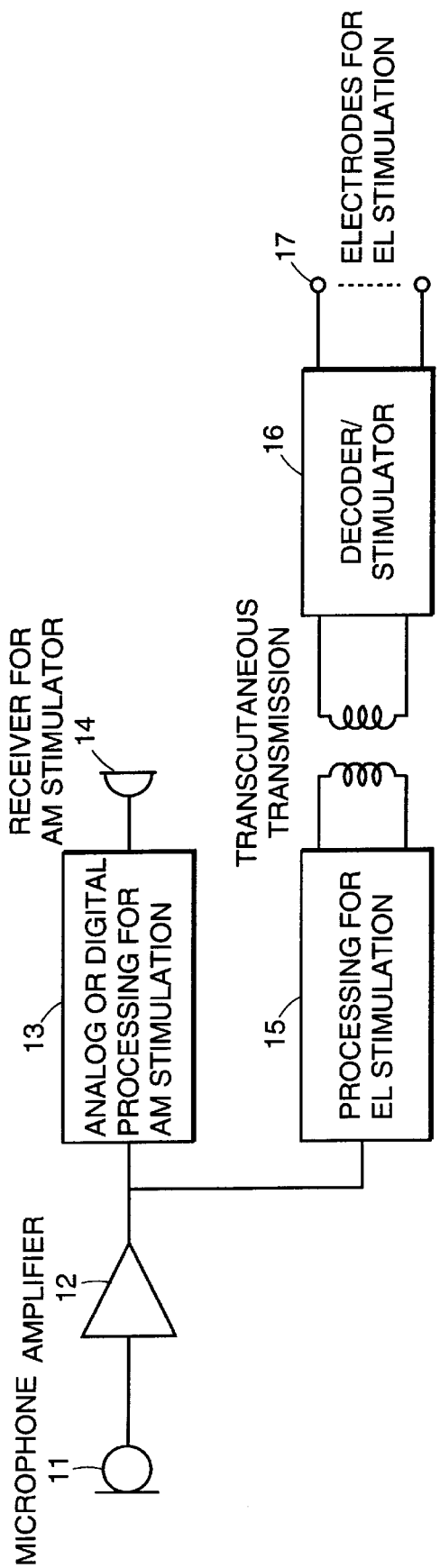
FIG. 1 is a block diagram of a preferred embodiment of a combined acoustic mechanical and electrical stimulation hearing prosthesis.

In the prior art, the choice between acoustic mechanical stimulation and electrical stimulation depended solely upon the degree of hearing loss. Generally, acoustic mechanical stimulation was greatly preferred, since inserting electrical stimulation electrodes destroyed the structures of the inner ear. Electrical stimulation was indicated only for nearly complete deafness, or for residual hearing which did not result in useful speech understanding.

Acoustic mechanical stimulation results in significantly better hearing improvement in the lower and middle frequency ranges. However, in approximately 90% of cases, the loss of hair cells begins with the higher frequency areas or the basal region of the cochlea. Once the structures of the inner ear are destroyed, it is no longer possible to stimulate them acoustically. On the other hand, electrical stimulation is particularly effective at the nerve endings at the basal region of the cochlea. The fact that electrical stimulation improves higher tones while low frequencies are not as well reached is the result of inability to insert the electrode carrier to the apex of the cochlea.

Thus, with a high percentage of the moderately to severely hearing impaired, previously available acoustical hearing aids did not result in a satisfactory speech understanding due to hearing loss in the high frequencies. Electrical stimulation in the sense of an electrode inserted into the cochlea was also not an option for these patients due to the loss of residual hearing associated with this procedure.

A preferred embodiment of the present invention combines both acoustic mechanical stimulation and electrical stimulation. This combination of techniques produces significant advantages for a large group of hearing impaired patients, specifically those who are between moderately impaired and on the border of deafness. This strategy of combining two different prosthetic approaches depends on avoiding disruptive interference of the stimulation patterns and the consequent disruption of speech understanding. Similarly, the electrical stimulation should be coupled to the cochlea so that intact structures are not destroyed—the option for electrical stimulation alone at a later time via cochlear implantation should remain. It is also desirable that a preferred embodiment be integrated into a single device. In order to improve the acceptance by the patient the device should be small and easy to use.

Preliminary studies performed on the cochlea of a cat have shown that the simultaneous application of both stimulation strategies does not fundamentally change the stimulation pattern at the auditory nerve. As has been proven by earlier models of cochlear implants, extracochlear electrical stimulation can be effective, although the results achieved with complete deafness are not comparable to those achieved with intra-cochlear stimulation. When used in combination with acoustic mechanical stimulation, as in a preferred embodiment, extracochlear electrical stimulation with the residual hearing is sufficient.

Simultaneous acoustic mechanical stimulation and electrical stimulation, therefore, represents a significant improvement over the prior for those with moderate to severe hearing loss. It is now possible to offer this patient group a hearing device which results in significantly improved speech understanding.

After complete ENT diagnostics and extensive testing of a patient's hearing ability, a conventional hearing aid must be tested and possibly refit. In the event that the objective speech testing demonstrates significant deficiencies in spite of optimal fitting of the hearing aid, the combined electric-acoustic stimulator would be indicated. Typical examples of patient groups who would benefit from the combined acoustic mechanical and electrical strategy as compared to currently available hearing aids include:

Adults with moderate to severe inner ear hearing losses on both sides with significant hearing losses in the frequency ranges over 1,000 Hz. This type of damage profile occurs for example after noise or physical trauma, head injury, drug induced intoxication (antibiotics, diuretics, chemotherapeutics, etc.), or after repeated challenge to the hearing.

Adult patients with progressive hearing loss related to age.

Children with bilateral congenital inner ear hearing losses in the high frequency range, after skull trauma or after toxic inner ear damage as above.

FIG. 1 is a block diagram of a preferred embodiment of a combined acoustic mechanical and electrical stimulation hearing prosthesis. An acoustic environment exists in the vicinity of a user. The sounds in the acoustic environment are distributed throughout a wide range of audio frequencies. A microphone 11 converts the sounds of the user's acoustic environment into a representative electrical signal output. The signal from the microphone 11 may be further processed by a stimulation amplifier 12 that produces an amplified representative electrical signal.

An acoustic mechanical stimulation module 13 receives the amplified representative electrical signal. The structure and operation of the acoustic mechanical stimulation module 13 may be as in a conventional hearing aid and employ either analog or digital signal processing. The output of the acoustic mechanical stimulation module 13 is a mechanical stimulation signal that, in a preferred embodiment, is representative of a subrange of low- to mid-range frequencies in the range of audio frequencies in the acoustic environment. The mechanical stimulation signal is delivered to the inner ear structure of the user by an acoustic mechanical stimulator receiver 14 that also may be as in a conventional hearing aid.

Figure 2:
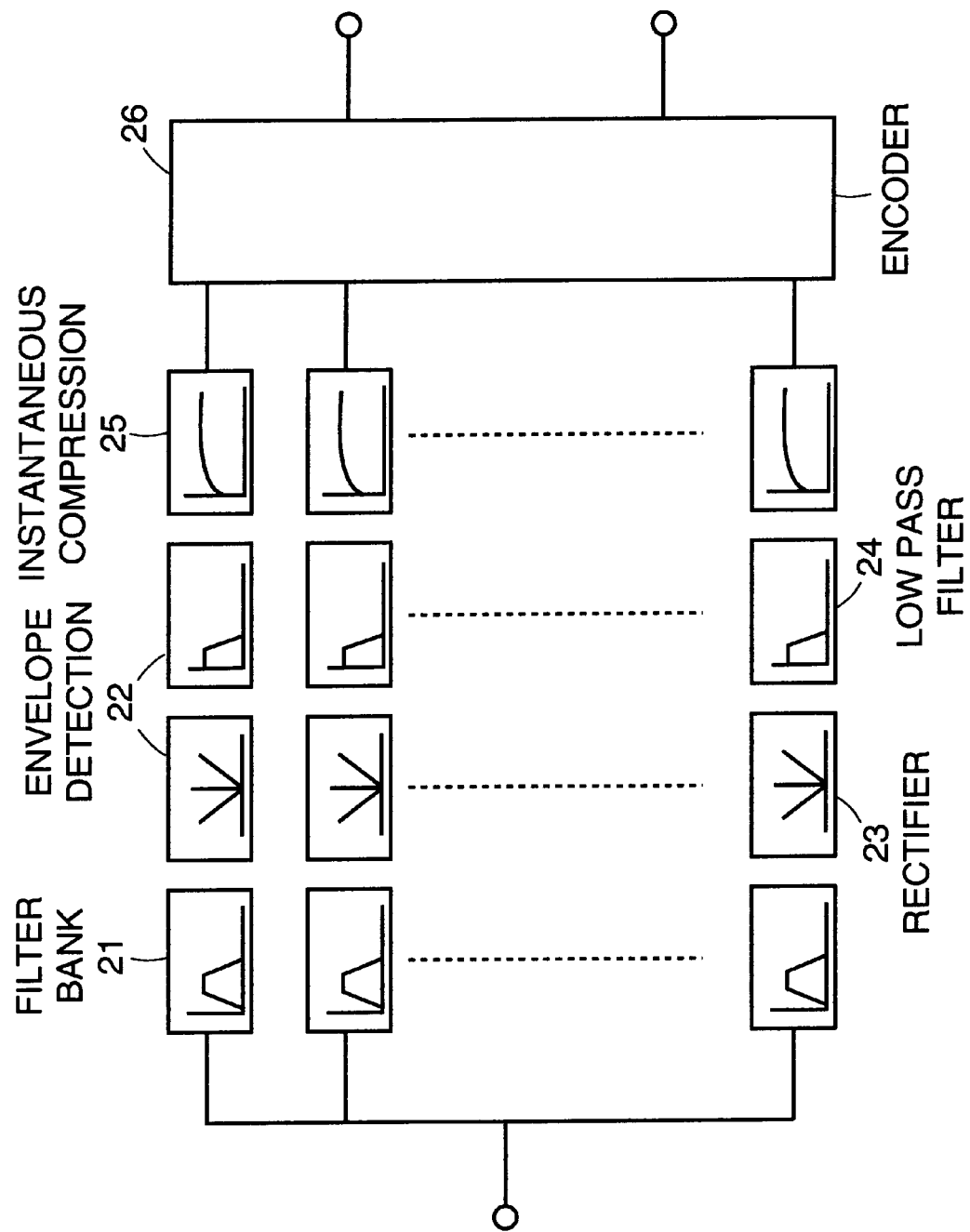
FIG. 2 is a block diagram of an electrical stimulation module employing CIS.

An electrical stimulation module 15 also receives the amplified representative electrical signal from the stimulation amplifier 12. The electrical stimulation module 15 uses either analog of digital signal processing to produce an electrical stimulation signal representative of a subrange of mid- to high-range frequencies in the range of audio frequencies in the acoustic environment Continuous interleaved sampling (CIS) is an example of a specific digital processing technique that is well-known in the field of hearing prosthesis systems. FIG. 2 is a block diagram of an electrical stimulation module employing CIS. The representative electrical signal input is first processed by a filter bank 21 of multiple band pass filters. Each bandpass filter passes a different relatively narrow band of frequencies from the subrange of frequencies processed by the electrical stimulation module 15. For each filter band, an amplitude of the filter band frequency envelope is extracted by an envelope detector 22 which may be a rectifier 23 in series with a low pass filter 24. The frequency envelope from each filter band then is processed by an instantaneous compressor 25 to form an amplitude modulated pulse which an encoder 26 multiplexes into the electrical stimulation signal for transcutaneous transmission.

The electrical stimulation signal from the electrical stimulation module, 15 in FIG. 1, is transcutaneously transmitted to a subcutaneous decoder stimulator 16 and delivered to the auditory nerve of the user by stimulation electrodes 17. The stimulation electrodes 17 may be multiple electrodes arranged in a multichannel array on one or more electrode carriers. In a preferred embodiment, the stimulation electrodes 17 may be placed in the close vicinity of the auditory nerve, but external to the cochlea. In other embodiments, the stimulation electrodes 17 may be inserted partially or fully into the cochlea either directly, or through one or more cochleostomy windows.

Figure 3A:
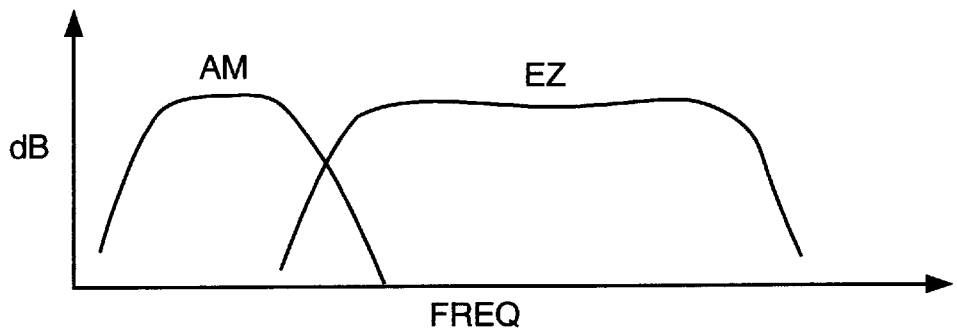
FIGS. 3(a)–(c) illustrates adjustment strategies for calibrating the stimulation signals in a preferred embodiment.
Figure 3B:
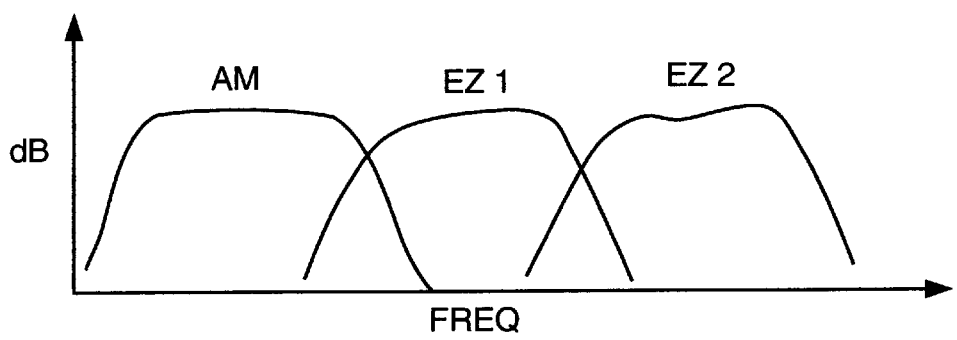
Figure 3C:
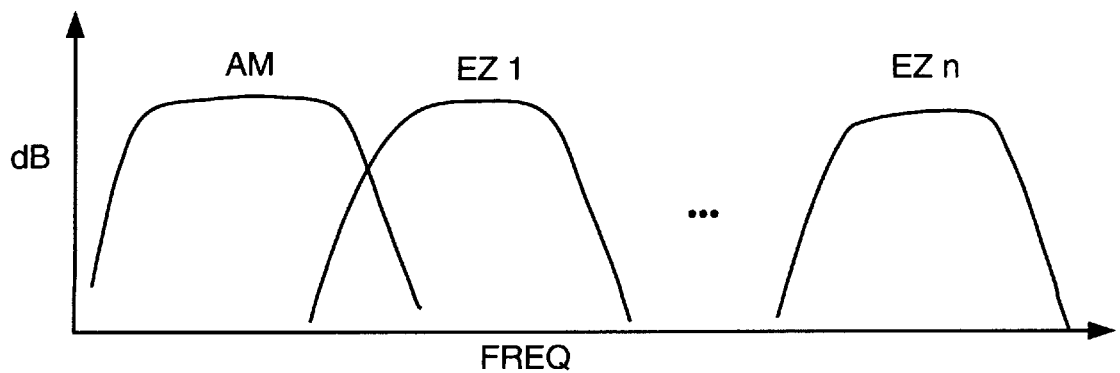

FIGS. 3(a)–(c) illustrates adjustment strategies for calibrating the stimulation signals in a preferred embodiment. In FIG. 3, the horizontal axis represents frequency, which increases towards the right, and the vertical axis represents amplification measured in decibels (dB). In each of FIGS. 3(a)–(c), it can be seen that the stimulation signal from the acoustic mechanical module is concentrated in the low- to mid-range of audio frequencies, while the stimulation signal (s) from the electrical stimulation module is concentrated in the mid- to -high-range of audio frequencies. As can be seen from FIGS. 3(a)–(c), the combination of acoustic mechanical stimulation and electrical stimulation covers more of the audio frequency than either would separately.

FIG. 3(a) shows the calibration adjustment for an embodiment producing a single channel of electrical stimulation which covers the mid- to high-range of audio frequencies. FIG. 3(b) shows an embodiment having two electrical stimulation channels one of which, EL1, covers the mid-range of audio frequencies and the other of which, EL2, covers the high-range of audio frequencies. FIG. 3(c) shows an embodiment having n multiple channels of electrical stimulation, EL1–ELn, such as would result from CIS processing.

The combination device of a preferred embodiment includes an acoustic mechanical component similar that found in prior art hearing aids and including a microphone, amplifier, and receiver; and, an electrical component for electrical stimulation of the cochlea and including a microphone, signal processing unit, signal encoder, transcutaneous link for signal and power transmission, implanted decoder/stimulator, and electrodes. The electrodes can, depending on the indication, include 1 or 2 electrodes for extra-cochlear placement, placement into cochleostomy windows, shallow intra-cochlear placement, or a multi-channel electrode for gentle intra-ochlear placement.

The acoustic mechanical component and the electrical component of a preferred embodiment can be combined in such a way that one or more of the following components may be common to both parts of the system: the microphone, the amplifier, the power supply, the case, a remote control and/or other electronic circuitry. One embodiment includes an ear-level device containing the extra-corporal parts, i.e., for in the ear or behind the ear placement. In another embodiment, the acoustic mechanical stimulation component and/or the electrical stimulation component may be fully implantable and encapsulated in two separate or one single common case.

What is claimed is:

1. A hearing prosthesis for a user in an acoustic environment having a range of audio frequencies, the prosthesis comprising:
    a microphone that converts the sounds of the acoustic environment into a representative electrical signal output;
    an electrical stimulation module responsive to the representative electrical signal that delivers to the auditory nerve of the user an electrical stimulation signal representative of a first subrange of frequencies in the range of audio frequencies in the acoustic environment; and
    an acoustic mechanical stimulation module responsive to the representative electrical signal that delivers to the inner ear structure of the user a mechanical stimulation signal representative of a second subrange of frequencies in the range of audio frequencies in the acoustic environment.

2. A hearing prosthesis according to claim 1, wherein the electrical stimulation module uses analog signal processing to produce the electrical stimulation signal.

3. A hearing prosthesis according to claim 1, wherein the electrical stimulation module uses digital signal processing to produce the electrical stimulation signal.

4. A hearing prosthesis according to claim 3, wherein the digital signal processing includes continuous interleaved sampling (CIS).

5. A hearing prosthesis according to claim 1, wherein the electrical stimulation module uses extracochlear electrodes to deliver the electrical stimulation signal.

6. A hearing prosthesis according to claim 5, wherein the extracochlear electrodes have a fixation collar.

7. A hearing prosthesis according to claim 5, wherein the extracochlear electrodes are ball-shaped or cone-shaped.

8. A hearing prosthesis according to claim 1, wherein the electrical stimulation module uses cochleostomy window-associated electrodes to deliver the electrical stimulation signal.

9. A hearing prosthesis according to claim 8, wherein the cochleostomy window-associated electrodes have a fixation collar.

10. A hearing prosthesis according to claim 8, wherein the cochleostomy window-associated electrodes are ball-shaped or cone-shaped.

11. A hearing prosthesis according to claim 1, wherein the electrical stimulation module uses multichannel array electrodes partially inserted into the cochlea of the user to deliver the electrical stimulation signal.

12. A hearing prosthesis according to claim 1, wherein the electrical stimulation module uses multichannel array electrodes fully inserted into the cochlea of the user to deliver the electrical stimulation signal.

13. A hearing prosthesis according to claim 1, wherein the acoustic mechanical stimulation module uses analog signal processing to produce the mechanical stimulation signal.

14. A hearing prosthesis according to claim 1, wherein the acoustic mechanical stimulation module uses digital signal processing to produce the mechanical stimulation signal.

15. A hearing prosthesis according to claim 1, further including a stimulation amplifier that amplifies the representative electrical signal output from the microphone for input to the stimulation modules.

16. A method of a hearing prosthesis system for processing sounds in an acoustic environment having a range of audio frequencies, the method comprising:
    converting, with a microphone, the sounds of the acoustic environment into a representative electrical signal output;
    delivering to the auditory nerve of a user, an electrical stimulation signal from an electrical stimulation module responsive to the representative electrical signal, the electrical stimulation signal representative of a first subrange of frequencies in the range of audio frequencies in the acoustic environment; and
    delivering to the inner ear structure of the user, a mechanical stimulation signal from an acoustic mechanical stimulation module responsive to the representative electrical signal, the mechanical stimulation signal representative of a second subrange of frequencies in the range of audio frequencies in the acoustic environment.

17. A method according to claim 16, wherein the electrical stimulation signal is produced by the electrical stimulation module using analog signal processing.

18. A method according to claim 16, wherein the electrical stimulation signal is produced by the electrical stimulation module using digital signal processing.

19. A method according to claim 18, wherein the digital signal processing includes continuous interleaved sampling (CIS).

20. A method according to claim 16, wherein the electrical stimulation module delivers the electrical stimulation signal using extracochlear electrodes.

21. A method according to claim 20, wherein the extracochlear electrodes have a fixation collar.

22. A method according to claim 20, wherein the extracochlear electrodes are ball-shaped or cone-shaped.

23. A method according to claim 16, wherein the electrical stimulation module delivers the electrical stimulation signal using cochleostomy window-associated electrodes.

24. A method according to claim 23, wherein the cochleostomy window-associated electrodes have a fixation collar.

25. A method according to claim 23, wherein the cochleostomy window-associated electrodes are ball-shaped or cone-shaped.

26. A method according to claim 16, wherein the electrical stimulation module delivers the electrical stimulation signal using multichannel array electrodes partially inserted into the cochlea of the user.

27. A method according to claim 16, wherein the electrical stimulation module delivers the electrical stimulation signal using multichannel array electrodes fully inserted into the cochlea of the user.

28. A method according to claim 16, wherein the mechanical stimulation signal is produced by the acoustic mechanical stimulation module using analog signal processing.

29. A method according to claim 16, wherein the mechanical stimulation signal is produced by the acoustic mechanical stimulation module using digital signal processing.

30. A method according to claim 16, further including amplifying the representative electrical signal output from the microphone with a stimulation amplifier for input to the stimulation modules.

* * * * *